(12) United States Patent
Weaver et al.

(10) Patent No.: US 10,495,549 B1
(45) Date of Patent: Dec. 3, 2019

(54) GEOLOGICAL SAMPLE PROCUREMENT AND STORAGE DEVICE

(71) Applicants: Christopher Michael Weaver, Tampa, FL (US); Eva Fernandez, Temple Terrace, FL (US); Brant Meier, Lakeland, FL (US); Brittany Elizabeth Mott, Cocoa Beach, FL (US); Christopher Allan Willis, Tampa, FL (US)

(72) Inventors: Christopher Michael Weaver, Tampa, FL (US); Eva Fernandez, Temple Terrace, FL (US); Brant Meier, Lakeland, FL (US); Brittany Elizabeth Mott, Cocoa Beach, FL (US); Christopher Allan Willis, Tampa, FL (US)

(73) Assignee: University of South Florida, Tampa, FL (US)

( * ) Notice: Subject to any disclaimer, the term of this patent is extended or adjusted under 35 U.S.C. 154(b) by 173 days.

(21) Appl. No.: 15/852,351

(22) Filed: Dec. 22, 2017

Related U.S. Application Data (60) Provisional application No. 62/437,866, filed on Dec. 22, 2016.

(51) Int. Cl.
    *G01N 1/08*      (2006.01)
    *G01N 33/24*      (2006.01)

(52) U.S. Cl.
    CPC .......... *G01N 1/08* (2013.01); *G01N 2033/245* (2013.01)

(58) Field of Classification Search
    CPC ....................................... G01N 1/08
    USPC ........................................ 73/864.31
    See application file for complete search history.

(56) References Cited

U.S. PATENT DOCUMENTS

| | | | |
|---|---|---|---|
| 4,257,268 A | * | 3/1981 | Pepicelli ............... B01L 3/0224 422/925 |
| 4,281,066 A | | 7/1981 | Thran et al. |
| 5,123,274 A | | 6/1992 | Carroll et al. |
| 5,921,328 A | | 7/1999 | Babineau et al. |
| 6,125,948 A | | 10/2000 | David et al. |
| 6,363,803 B1 | | 4/2002 | Hubers |
| 7,854,707 B2 | | 12/2010 | Hibner et al. |
| 7,896,817 B2 | | 3/2011 | Garrison |
| 8,771,200 B2 | | 7/2014 | Thompson et al. |

(Continued)

FOREIGN PATENT DOCUMENTS

JP      3436671 B2      8/2003

*Primary Examiner* — Tarun Sinha
(74) *Attorney, Agent, or Firm* — Nicholas Pfeifer; Smith & Hopen, P.A.

(57) ABSTRACT

A sample procurement and retention tool designed for extraterrestrial use. The device is adapted to procure and retain multiple loosely adhered geological samples of various shapes, sizes, and weights. In addition, the device is sized for dexterity optimization, and designed to prevent cross contamination of samples. The device includes a chamber housing detachable from a handle assembly with a portion of the chamber housing being rotatable with respect to the handle assembly. The chamber housing includes a plurality of chambers with at least one chamber having a sample cartridge that can be triggered through the handle assembly. Each sample cartridge stored in the chambers can be triggered to retrieve samples and then the chamber housing can be detached to employ another chamber housing.

20 Claims, 12 Drawing Sheets

(56) References Cited

U.S. PATENT DOCUMENTS

| | | | |
|---|---|---|---|
| 9,200,492 B2 | 12/2015 | McGraw | |
| 9,414,814 B2 | 8/2016 | Hibner et al. | |
| 2013/0272085 A1* | 10/2013 | Quinto | B29B 7/22 366/76.7 |

* cited by examiner

GEOLOGICAL SAMPLE PROCUREMENT AND STORAGE DEVICE

CROSS-REFERENCE TO RELATED APPLICATIONS

This application claims priority to provisional application No. 62/437,866, entitled "GEOLOGICAL SAMPLE PROCUREMENT AND STORAGE DEVICE," filed Dec. 22, 2016 by the same inventors.

BACKGROUND OF THE INVENTION

1. Field of the Invention

This invention relates, generally, to sample procurement and storage devices.

2. Brief Description of the Prior Art

Currently, there is a need for an extraterrestrial sample procurement and storage device that is operational in minimal gravity environments and in any atmosphere. The device should include a simple and efficient way to procure multiple samples and sealingly store the procured samples.

However, in view of the art considered as a whole at the time the present invention was made, it was not obvious to those of ordinary skill in the field of this invention how to achieve these objectives.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a simple and efficient sample procurement and storage device is now met by a new, useful, and nonobvious invention.

The novel structure includes a handle assembly and a chamber housing, which are detachable from each other in an embodiment. The handle assembly includes a trigger having a distal end and a proximal end and a rotational axle disposed therebetween. The handle assembly also includes a handle that receives the rotational axle.

a deck plate is in mechanical communication with the handle and includes an aperture sized to receive a quick-release pin. The deck plate is also in mechanical communication with an alignment member that extends at least partially through the deck plate. The deck plate further includes guide receipts for receiving guide supports extending from a cover plate.

The chamber housing includes a base plate and a plurality of chambers attached thereto. The base plate includes a central aperture for receiving. The base plate further includes an alignment member receipt to at least partially receive a portion of the alignment member when the alignment member extends through the deck plate.

An embodiment also includes an end plate at the distal ends of the chambers. The end plate has a central aperture axially aligned with the central aperture in the base plate and the end plate and base plate are rotationally fixed with respect to each other.

The device may also include a cover plate disposed in overlying and abutting relation to a distal surface of the end plate. The cover plate has a central aperture axially aligned with the central aperture in the end plate and a fastener passes through the central aperture in the cover plate and the central aperture in the end plate in a rotationally free manner, such that the end plate remains free to rotate with respect to, collectively, and chambers extending therebetween.

The cover plate further includes a guide member extending in a proximal direction and sized to be received by the guide receipt in the deck plate. The guide member prevents rotation between the cover plate and the deck plate. Thus, the collection of the cover plate, base plate, and chambers is free to rotate with respect to the handle assembly and the cover plate.

A trigger action pin is in mechanical communication with a distal end of the trigger such that actuation of the trigger causes translation of the trigger action pin towards the chamber housing. The deck plate also includes an aperture that is axially aligned with the trigger action, to receive the trigger action pin when it translates towards the chamber housing. The rotatable base plate also includes trigger pin receiving apertures, each adapted to receive the trigger action pin when axially aligned with the trigger action pin.

The chamber housing includes a plurality of chambers with a sample cartridge disposed within at least one of the plurality of chambers. A distal end of the sample cartridge is configured to pass through a chamber aperture in the end plate, that is axially aligned with the trigger action pin, when the trigger action pin translates into the chamber through the trigger pin receiving aperture.

An embodiment includes a rotational bearing disposed in the central aperture in the end plate and a bearing disposed in the central aperture in the base plate.

An embodiment includes at least one of the plurality of chambers being a designated empty chamber that does not include a sample cartridge. The designated empty chamber may include an attachment hard point adapted to mechanically attach to a lanyard.

In an embodiment, the quick release pin has a position of repose and a release position. In the position of repose, a distal end of the pin extends through the central apertures in the deck plate and the base plate. In the release position, the distal end of the pin does not protrude through the central aperture in the base plate, thereby allowing the chamber housing to be separated from the handle assembly.

An embodiment further includes chamber seals disposed at the distal end of each chamber, thereby sealing the chambers when the chamber seals are in abutting relation to the cover plate.

In an embodiment, the sample cartridge includes a first plunger configured to be acted upon by the trigger action pin when the trigger action pin is axially aligned with the trigger pin receiving aperture and a user actuates the trigger. The sample cartridge may also include a second plunger with a cartridge function spring disposed between the first and second plungers. A cartridge extension spring extends between the second plunger and a distal flange. Whereby the translation of the trigger action pin through the trigger pin receiving aperture causes the trigger action pin to contact the first plunger, which causes the sample cartridge to open at a distal end, and further translation of the trigger action pin causes the first plunger to force the second plunger in a distal direction, which causes the distal end of the cartridge to extend through the aperture in the cover plate.

An embodiment includes a locking mechanism adapted to prevent rotation between the cover plate and collectively the base plate, chambers, and end plate.

An object of the invention is to provide a device that is simple to use that can efficiently procure and sealingly store multiple samples.

Another object of the invention is to provide a device adapted to procure and independently store geological or extraterrestrial samples in an isolated manner.

A further object of the invention is to provide an extraterrestrial sample procurement and storage device that is operational in minimal gravity environments and in any atmosphere.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention was developed to answer the need of sampling geological specimens once astronauts travel to an asteroid orbiting around the moon, however, the device can be used in any environment to collect any sample. The device procures and stores geological samples until they are removed from cross contamination-proof sample cartridges to be tested and analyzed.

An embodiment of the device includes simple pistol-style grip and trigger designed for ambidextrous use. The device further includes a replaceable chamber housing configured to revolve during use. In an embodiment, the chamber housing has a plurality of sampling chambers and one dummy chamber. An embodiment includes lanyard attachment locations for the handle assembly and the chamber housing. Moreover, the sampling chambers of the chamber housing are designed to be interchangeable prior to a sampling session depending on the desired method(s) of sample procurement including, but not limited to: obtaining a single solid float sample between 0.25 inches and 1.5 inches in diameter, a soil sample, a core sample, and environmental probe. Furthermore, the sampling chambers may be transparent and marked with an identifying feature, such as a number.

During use, the operator selects one of the sampling chambers by rotating the revolving chamber housing in either direction to bring the desired chamber into the active position. The chamber housing is designed to lock firmly into position whenever any chamber is in the active position. To retrieve a sample, the operator actuates the trigger on the handle assembly at which point, depending on the engaged sampling method, different apparatuses will protrude from the distal end of the device. For procuring a single solid float sample, sampling claws will extend and expand; for obtaining a soil sample, a sectioned bucket will extend and open; for core sampling, a core drill will extend while rotating; or for environmental probing, a probe will extend. Upon releasing the trigger, with the sample procured in the sampling apparatus or probe reading acquired, the sampling apparatus will return back into the chamber housing and the act of sample retrieval or environmental reading is complete. The operator then rotates the housing chamber to a remaining available sampling chamber and the act of retrieving a sample can be repeated. When the last sampling chamber has been used, the chamber housing is rotated to place the dummy chamber in the active position (axially aligned with the trigger action pin) as to ensure all acquired samples are securely contained and isolated in their respective chambers.

The sampling cartridge may be replaced by pulling the quick-release pin located just forward of the trigger. In an embodiment, the quick-release pin does not need to be fully removed from the handle assembly to separate the chamber housing from the handle assembly. Inside the dummy chamber is a D-ring for lanyard attachment when the dummy chamber is in the active position. Once the chamber housing has been secured with a lanyard, the operator can then pull the quick-release pin until it has fully disengaged from the chamber housing and separate the chamber housing from the handle assembly.

To attach a new chamber housing, the operator must align the guide supports on the chamber housing with the guide sockets in the handle assembly, and while holding the chamber housing, insert the quick-release pin until it is fully engaged with the chamber housing. The operator can then separate the lanyard from the D-ring in the dummy chamber and the act of sample retrieval can continue.

Referring now to the detailed figures, an embodiment of the present invention includes handle assembly 10 and chamber housing 22, which are interconnected during operation, but remain separable for quickly and easily exchanging chamber housing 22 with another chamber housing.

Figure 1:
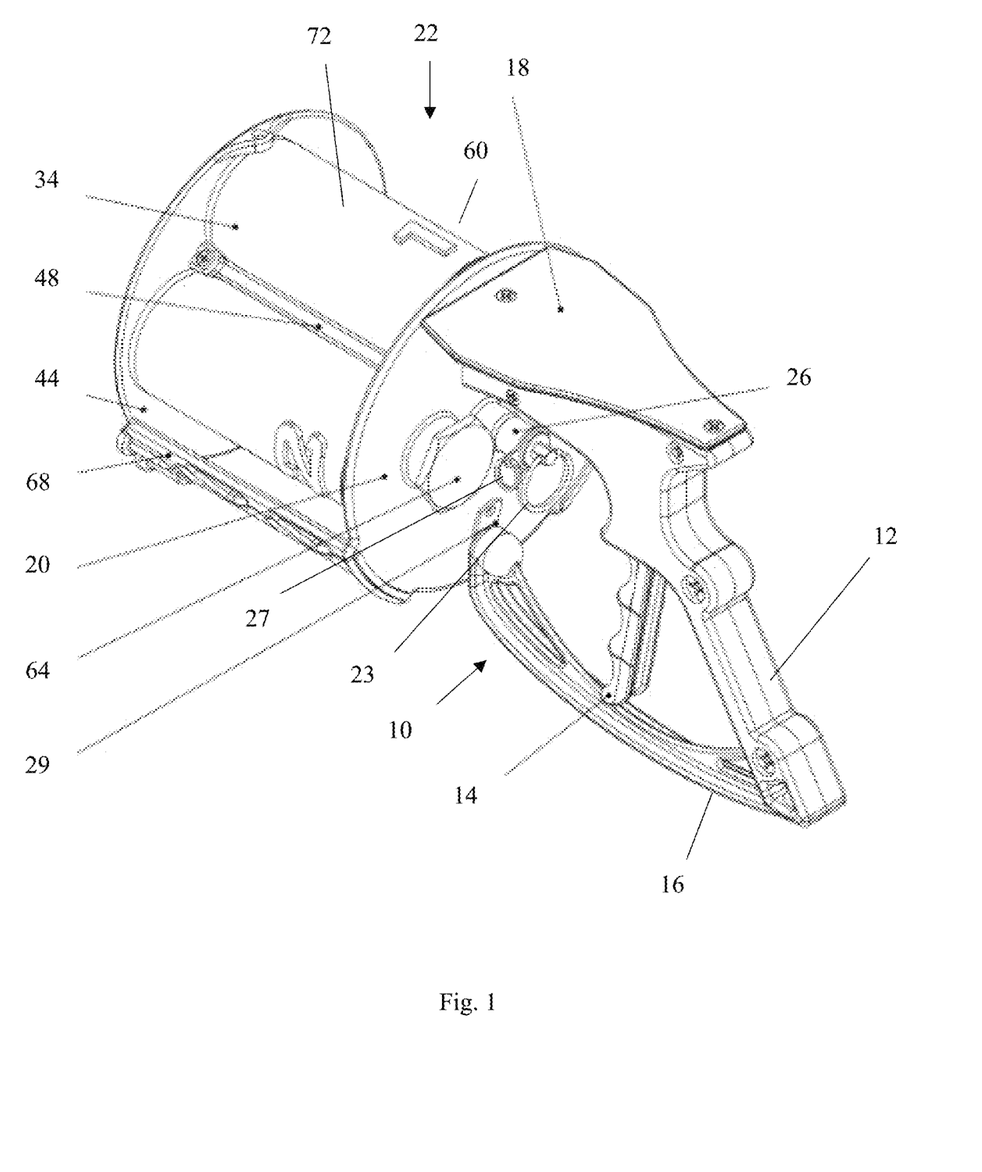
FIG. 1 is a rear perspective view of an embodiment of the present invention.
Figure 2:
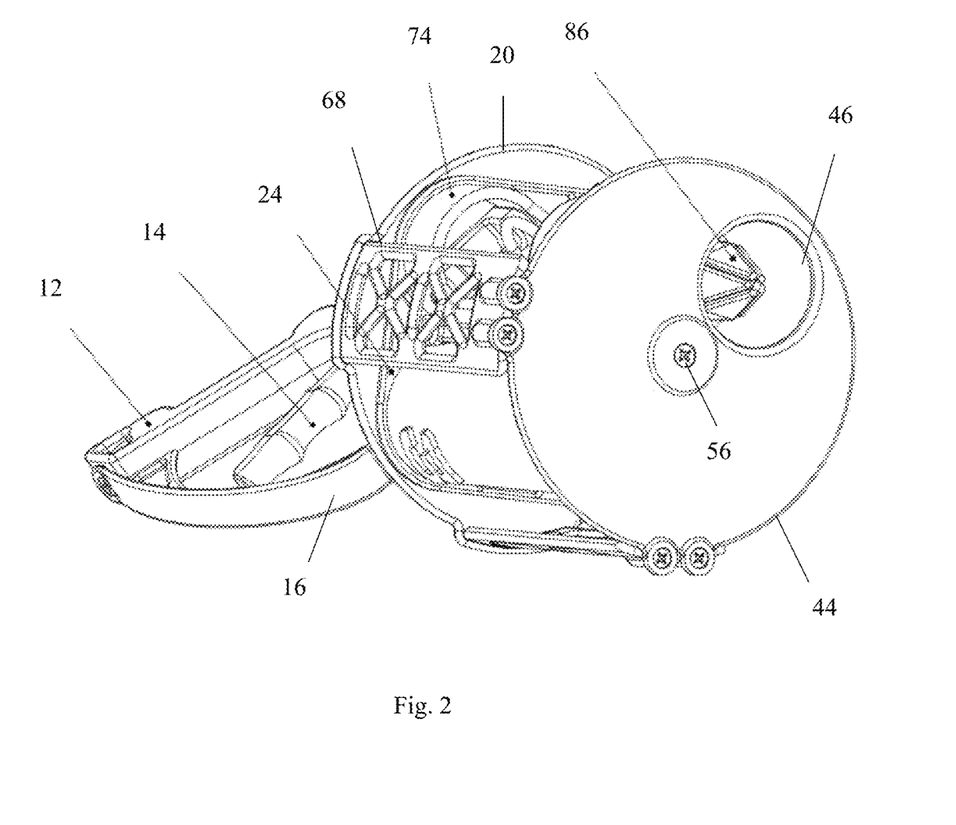
FIG. 2 is a front perspective view of an embodiment of the present invention.

As depicted in FIGS. 1-2, an embodiment of handle assembly 10 includes a pistol-style handle 12 in communication with trigger 14. The handle and trigger are preferably ambidextrous in design with finger/thumb grooves to provide comfort to the user. Handle assembly 10 further includes trigger guard 16 and top stabilizer 18 extending to deck plate 20. Trigger guard 16 and top stabilizer 18 provide the structural connections between deck plate 20 and the handle-trigger assembly. Trigger guard 16 provides the additional benefits associated with typical trigger guards, e.g. prevention of accidental trigger actuation.

Figure 3A:
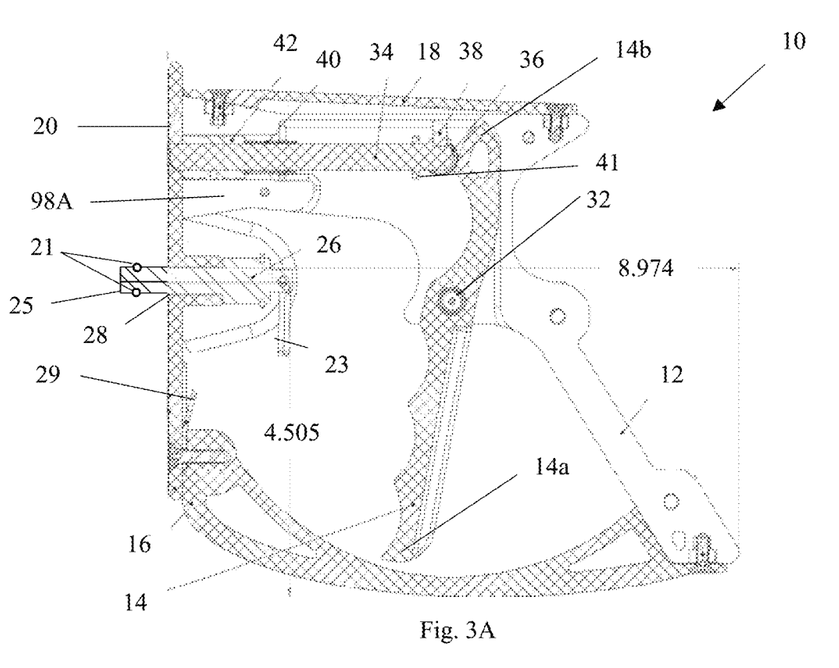
FIG. 3A is a side sectional view of an embodiment of the detached handle assembly of the present invention.
Figure 3B:
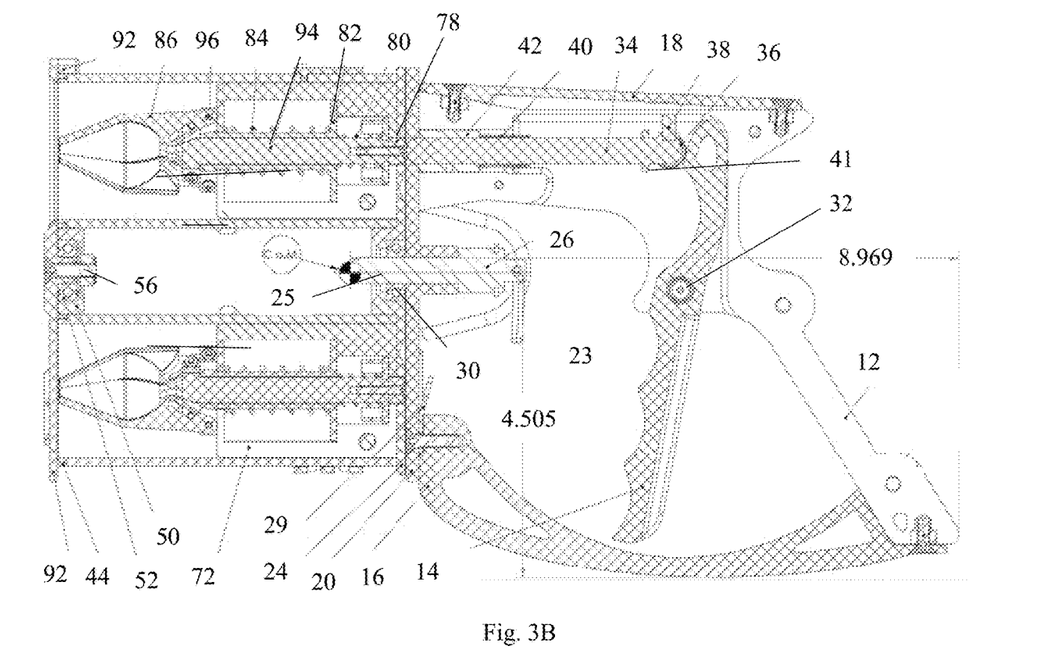
FIG. 3B is a side sectional view of an assembled embodiment of the present invention.
Figure 4:
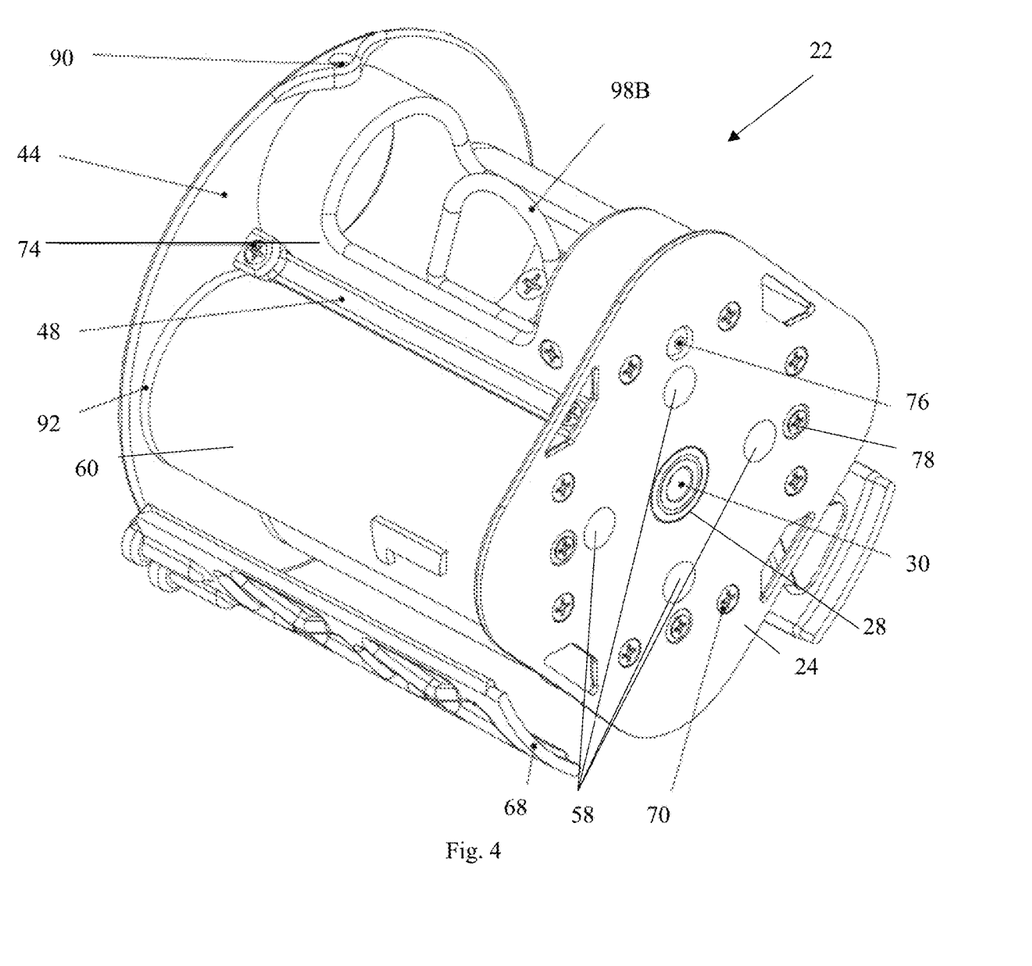
FIG. 4 is a rear perspective view of an embodiment of the detached chamber housing.
Figure 12:
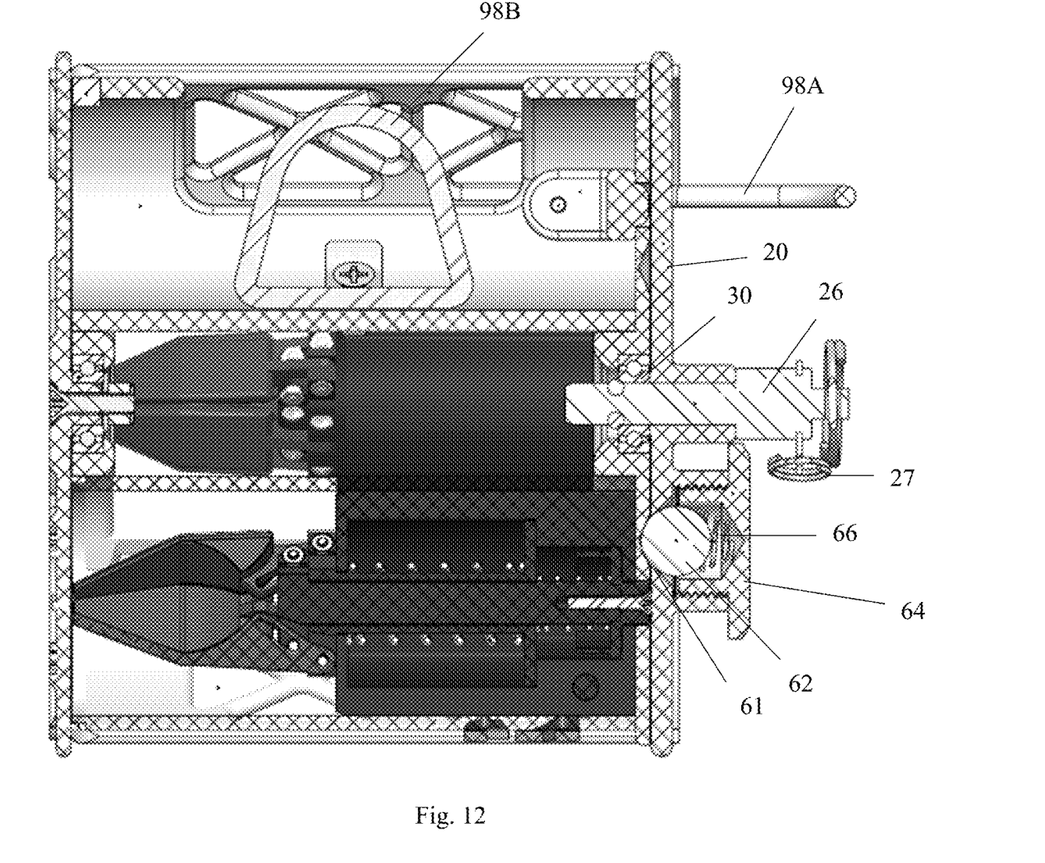
FIG. 12 is a cross-sectional view of an embodiment of the chamber housing.

Referring now to FIGS. 3-4 and 12, an embodiment of handle assembly 10 is detachable from chamber housing 22 through quick-release pin assembly 26. Quick-release pin 25 extends through deck plate 20 and inserts into chamber housing base plate 24 through pin receipt 28. Quick-release pin assembly 26 may be a conventional quick-release pin assembly. The depicted embodiment includes pull tab 23 for removing pin 25 by overcoming a biasing component within the quick-release pin assembly 26, such as a spring in mechanical communication with the quick-release pin and/or overcoming one or more detents 21 on a distal end of pin 25. Moreover, quick-release pin assembly 26 includes a lanyard attachment 27 (see FIG. 1) for receiving a lanyard (not shown). The lanyard may also be attached to lanyard clip 29 on deck plate 20.

As best illustrated in FIGS. 3B-4 and 12, quick-release pin 25 extends through bearing 30 disposed in pin receipt 28, when the device is fully assembled. Bearing 30 allows base plate 24 to freely rotate around quick-release pin 25. Thus, chamber housing 22 can be easily rotated to place a desired chamber into the active position—the position in which chamber 60 is axially aligned with trigger action pin 34.

FIG. 3 further depict the mechanics behind triggering the device. Moving vertically in view of FIG. 3A, trigger 14 includes a gripping section near first end 14a, pivot 32 upwards therefrom, and curved distal end 14b in contact with trigger action pin 34. Pivot 32 allows the trigger to act as a conventional lever to translate trigger action pin 34.

Figure 8A:
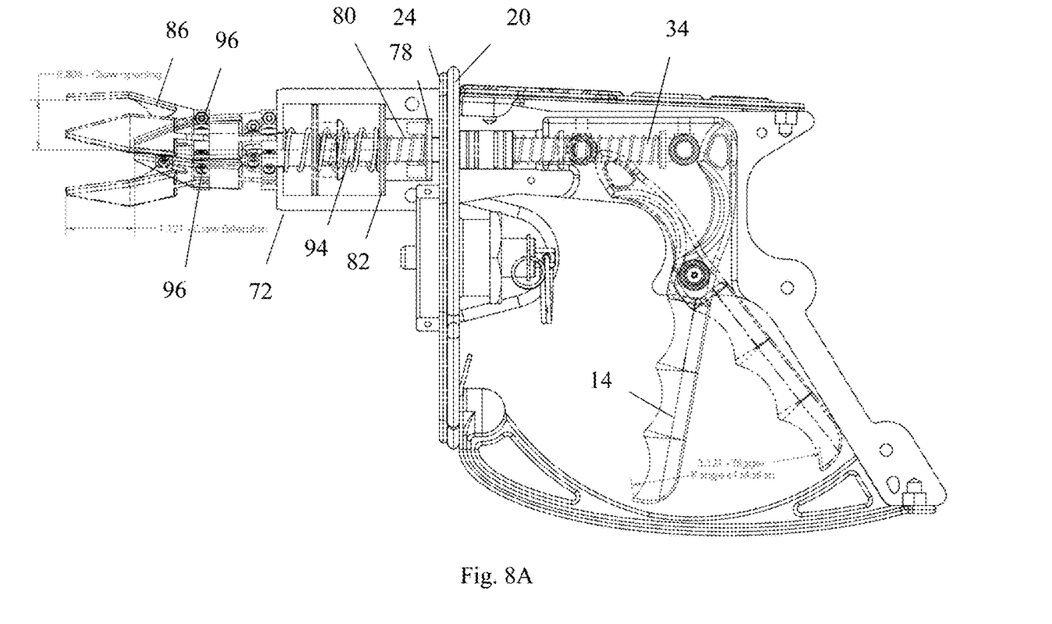
FIG. 8A is a side sectional view depicting the translation of the sampling feature when the trigger is actuated. The chamber housing has been removed to show the actuation of the internal components.

The distal end of trigger 14 has a curved contacting surface to better interact with rotational bearing 36 disposed on the proximal/back end of trigger action pin 34. As the proximal end or bottom end of trigger 14 is actuated towards grip 12, trigger 14 pivots about pivot 32 causing the distal end to travel along the circumference of rotational bearing 36 while trigger action pin 34 is translated towards chamber housing 22. This action is depicted in FIG. 8A. Rotational bearing 36 prevent binding and reduces friction between trigger action pin 34 and the upper distal end of trigger 14.

Referring back to FIG. 3, trigger action pin 34 includes guide pin 38 extending between the trigger action pin 34 and an upper surface of a cavity housing trigger action pin 34. Guide pin 38 helps maintain trigger action pin 34 in a desired axis of translation to prevent unwanted binding between trigger action pin 34 and the internal components surrounding trigger action pin 34.

Figure 7A:
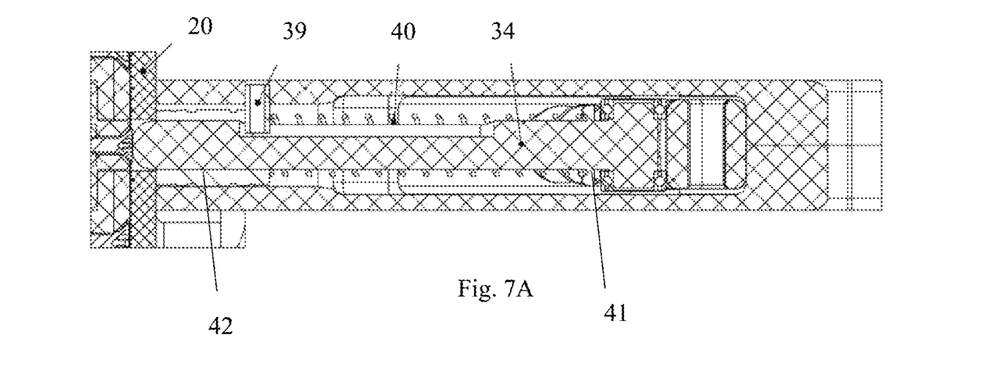
FIG. 7A is a cross-sectional view of an embodiment of the trigger action pin.
Figure 7B:
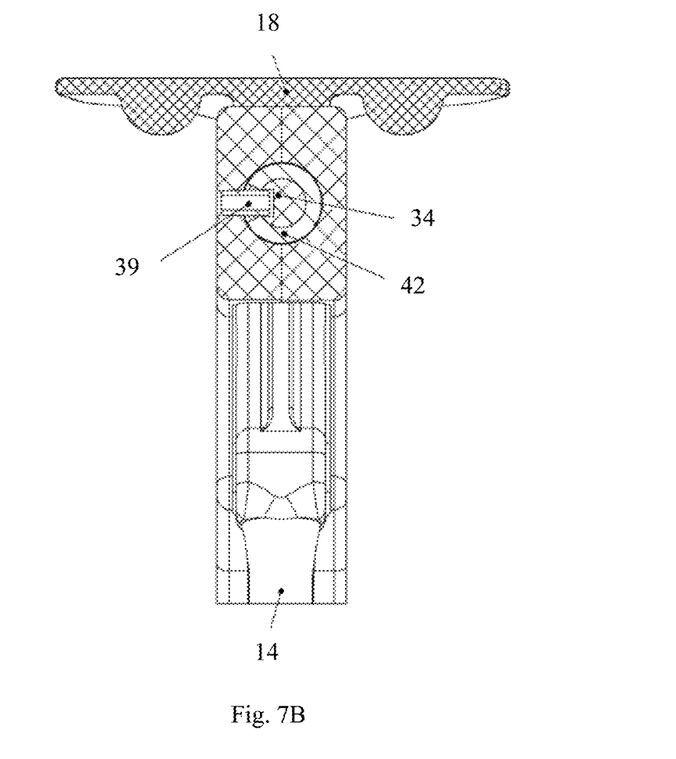
FIG. 7B is a rear cross-sectional view of an embodiment of the trigger action pin.

As depicted in FIG. 7, an embodiment of handle assembly 10 may also, or alternatively, include rolling pin 39 that extends sideways between trigger action pin 34 and the cavity housing trigger action pin 34. Rolling pin 39 also helps maintain trigger action pin 34 in a desired axis of translation to prevent unwanted binding between trigger action pin 34 and the internal components surrounding trigger action pin 34. FIG. 7 also depict linear bearing 42 in the shape of a ring. Linear bearing 42 received trigger action pin 34 and aids in keeping trigger action pin 34 concentrically aligned with linear bearing 42.

Trigger action pin 34 is preferably sized to prevent the distal end—the end opposite from the rotational bearing 36—from protruding from deck plate 20 when trigger action pin 34 is in a position of repose—the position shown in FIG. 3A. Trigger action pin 34 further includes trigger spring 40 that extends between spring supports 41 and bearing 42. Trigger spring 40 ensures that trigger action pin 34 returns to the position of repose after trigger 14 is disengaged, and bearing 42 reduces the friction during linear translation of trigger action pin 34. It should be noted that trigger spring 40 in in FIG. 3 is not shown as extending between linear spring 42 and spring supports 41 in an attempt to reduce congestion in the figures. The full spring is depicted in FIGS. 7A and 8A.

Referring now to FIGS. 3B-6, chamber housing 22 attaches to handle assembly 10 through both fixed connections and rotational connections. At a proximal end, chamber housing 22 includes base plate 24, which abuts deck plate 20 when the device is fully assembled. Bearing 30 in base plate 24 allows the rotational portion of chamber housing 22 to rotate about quick-release pin 25. At a distal end, chamber housing 22 has a non-rotational cover plate 44 to ensure that sampling aperture 46 remains axially aligned with trigger action pin 34.

Figure 5:
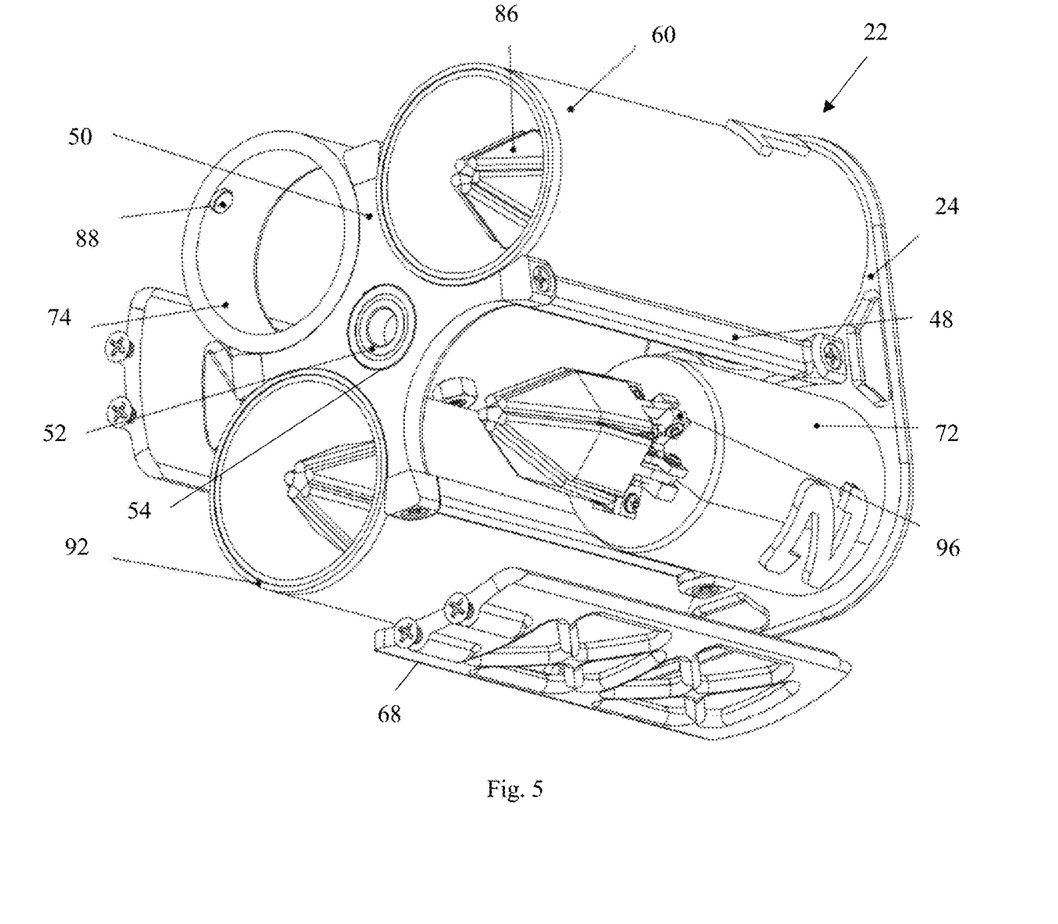
FIG. 5 is a front perspective view of an embodiment of the detached chamber housing with the cover plate and second chamber removed.

As best illustrated in FIGS. 4-5, base plate 24 includes support members 48 that extend towards cover plate 44 and attach to end plate 50. Thus, base plate 24 and end plate 50 will rotate together. End plate 50 includes rotational bearing 52 disposed in aperture 54. Rotational bearing 52 is axially aligned with bearing 30 in base plate 24 and receives fastener 56 (see FIGS. 3B and 8B), which secures cover plate 44 to end plate 50 in a rotationally-free manner. As a result, end plate 50, base plate 24, and the objects disposed therebetween remain free to rotate with respect to handle assembly 10 and cover plate 44.

Figure 6:
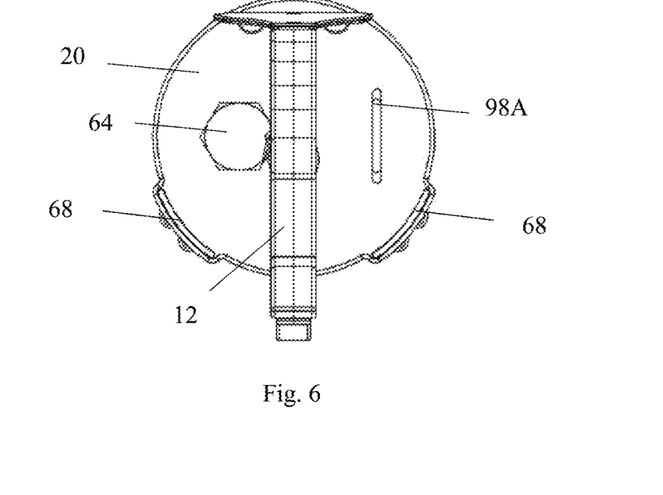
FIG. 6 is a rear view of an embodiment of the present invention.
Figure 8B:
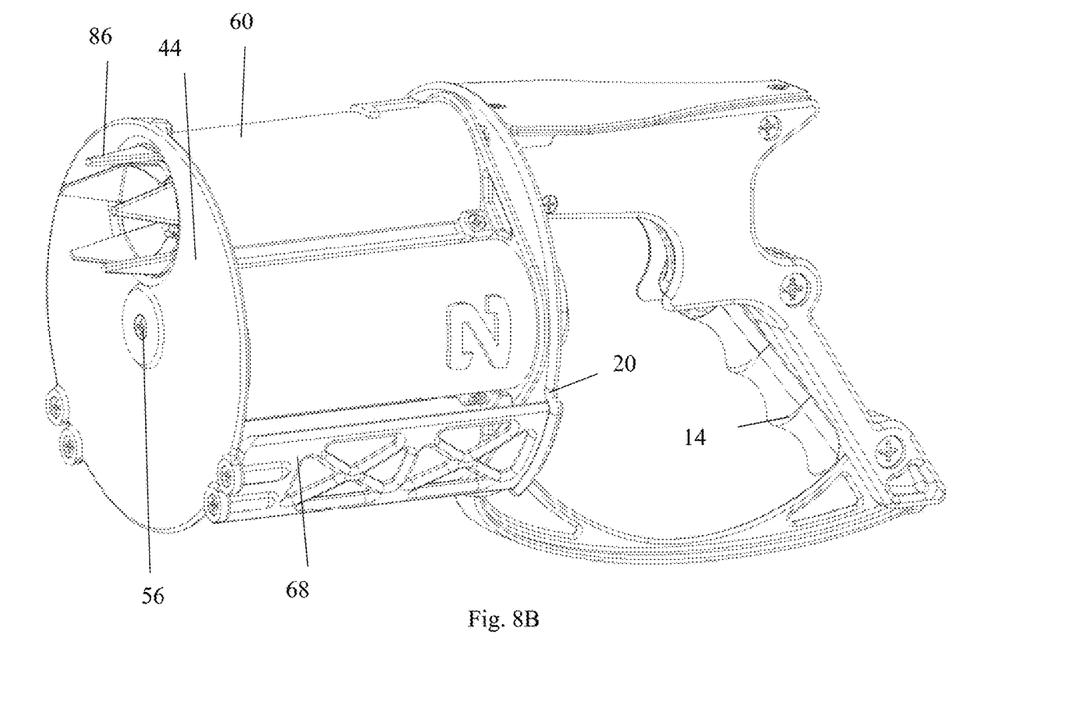
FIG. 8B is a front perspective view of an embodiment of the present invention showing the sampling feature extending at least partially from the chamber housing.

As best illustrated in FIGS. 4, 6, and 8B, cover plate 44 includes guide supports 68. Guide supports 68 extend from cover plate 44 towards handle assembly 10 and are received by deck plate 20. Guide supports 68 aid in securing a replacement chamber housing to the handle assembly. Once received by deck plate 20, guide supports 68 also prevent cover plate 44 from rotating with respect to the handle assembly 10 to ensure that sampling aperture 46 remains axially aligned with trigger action pin 34. End plate 50, base plate 24, and the objects disposed therebetween, however, remain free to rotate with respect to handle assembly 10 and cover plate 44.

As most clearly shown in FIG. 4, alignment divots 58 are disposed in the proximal surface—surface abutting deck plate 20—of base plate 24. In an embodiment, alignment divots 58 are centrally aligned about the longitudinal axis of chambers 60, which house the sampling devices. As most clearly depicted in FIG. 12, deck plate 20 includes alignment aperture 61 sized to partially receive alignment ball 62, such that a portion of alignment ball 62 extends beyond deck plate 20 in a distal direction. Thus, alignment ball 62 is received by alignment divots 58 when base plate 24 is rotated to a position in which one of the chambers 60 is axially aligned with trigger action pin 34. Alignment ball 62 is housed in chamber 64 and subjected to spring 66 forcing alignment ball 62 towards base plate 24.

There is preferably one alignment divot 58 for each chamber 60 and each alignment divot 58 is disposed in base plate 24 at specific locations to ensure that each chamber 60 will align with trigger action pin 34. The alignment ball is depicted as a spherical object; however, other shaped objects may be used. Preferably the portion that extends beyond deck plate 20 has a curved shape to reduce the friction when the alignment divots are rotated out of alignment with the alignment ball. The alignment ball will thus be referred to as an alignment member hereinafter.

Chamber housing 22 further includes a plurality of chambers 60 secured between base plate 24 and end plate 50. As shown in FIG. 4, each chamber 60 is secured to base plate 24 using fasteners 70. Fasteners 70 preferably also secure sample cartridge 72 to base plate 24.

Referring now to FIG. 5, end plate 50 is designed around chambers 60. In the embodiment provided, four cylindrical chambers 60 are secured to base plate 24, and therefore, end plate 50 includes four circular cutouts that house the distal ends of chambers 60. The overall shape of end plate 50 is dependent on the number of chambers, which may vary depending on the mission.

Referring back to FIG. 4, base plate 24 further includes apertures exposing the sample cartridge plungers 78, which are acted upon by trigger action pin 34 when chambers 60 are axially aligned with trigger action pin 34 and a user actuates trigger 14. As shown in FIG. 3B-4, each sample cartridge 72 includes a first proximal plunger 78. Referring to FIGS. 3B and 8A, plunger 78 is in communication with cartridge function spring 80, which is disposed between first plunger 78 and second plunger 82. Second plunger 82 is also in communication with a spring referred to as cartridge extension spring 84. In the embodiment shown, first plunger 78 opens claws 86 when cartridge function spring 80 is compressed and second plunger 82 extends opened claws 86 in a distal direction when extension spring 84 is compressed. FIG. 8A provides a view of the internal workings as the two plungers are compressed and FIG. 8B illustrates how the device as a whole would look when triggered.

As highlighted in FIG. 8A, actuation of trigger 14 forces trigger action pin 34 to translate through base plate 24 and into sample cartridge 72. Trigger action pin 34 forces first proximal plunger 78 in a distal direction. In the claw embodiment, proximal plunger 78 is in communication with sampling rod 94, which translates with proximal plunger 78. The distal end of sampling rod 94 contacts the curved flanges of claws 86 causing claws 86 to pivot open about pivoting axes 96. See FIG. 3B in conjunction with FIG. 8A.

As trigger action pin 34 continues to translate towards the distal end of the device, it further forces proximal plunger 78 towards second plunger 82. Once proximal plunger 78 contacts second plunger 82, trigger action pin 34 indirectly forces second plunger 84, which is in contact with claws 86 and forces said claws out of chamber 60.

In an embodiment, the maximum distance an operator will have to squeeze the trigger is 3.121 inches, which is consistent with other pistol grip, lever-operated devices of similar motion. This engagement distance translates to the sampling apparatus extending 1.21 inches.

The illustrated embodiments depict sampling cartridges having claws 86, but several other sampling features are considered. Depending on the engaged sampling method, different apparatuses will protrude from the distal end of the device; for procuring a single solid float sample, sampling claws will extend and expand; for obtaining a soil sample, a sectioned bucket will extend and open; for core sampling, a core drill will extend while rotating; or for environmental probing, a probe will extend.

In an embodiment, each chamber 60 includes a seal 92 located at the distal end of the chamber, which is depicted in FIG. 5. Chambers 60 remain in close proximity to cover plate 44 when not aligned with sampling aperture 46, such that seals 92 seal the chambers from the ambient environment. The seal ensures that samples are not contaminated after retrieval/during transport to a location for analysis.

Preferably one of the chambers is a designated empty chamber 74. Empty chamber 74 is provided so that a user can rotate the empty chamber into axial alignment with trigger action pin 34 to avoid accident actuation of sample cartridges 72. As depicted best in FIG. 4, empty chamber 74 includes a dummy cartridge access 76, which prevents trigger action pin 34 from passing through base plate 24.

Designated empty chamber 74 is further equipped with magnet 88, as shown in FIG. 5, which is magnetically attracted to magnet 90 disposed on cover plate 44, as shown in FIG. 4. The magnets ensure that designated empty chamber 74 remains aligned with sampling aperture 46 when chamber housing 22 is detached from handle assembly 10. In turn, the magnets ensure that chambers 60 remain sealed off from the ambient environment. An embodiment may use any other locking mechanism for preventing rotation of the chamber housing with respect to the handle assembly.

Figure 9:
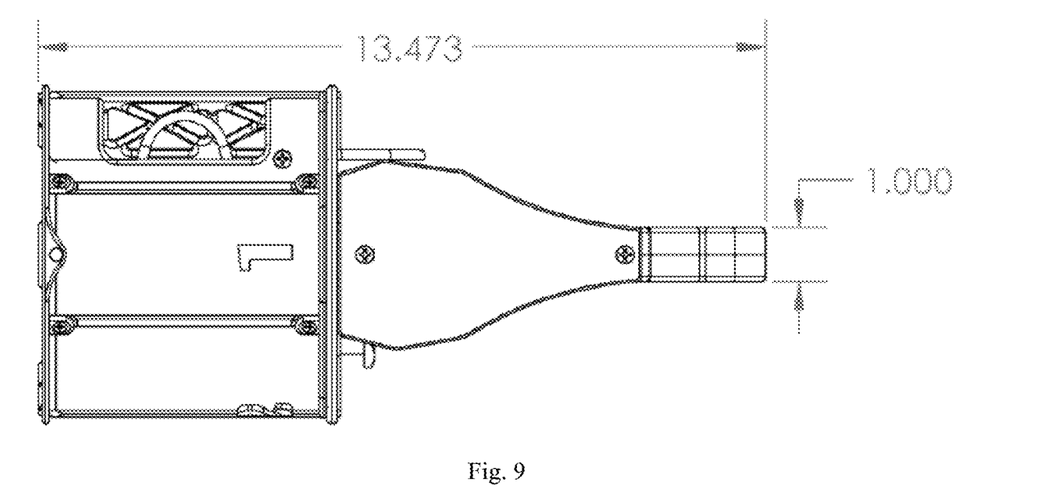
FIG. 9 is a top view of an embodiment of the present invention.
Figure 10:
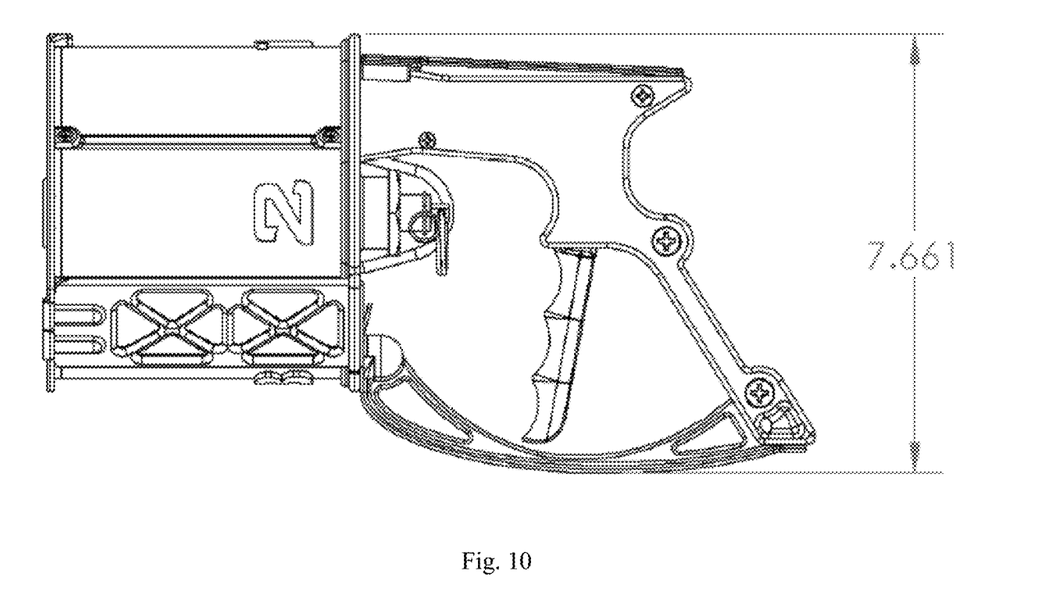
FIG. 10 is a side view of an embodiment of the present invention.
Figure 11:
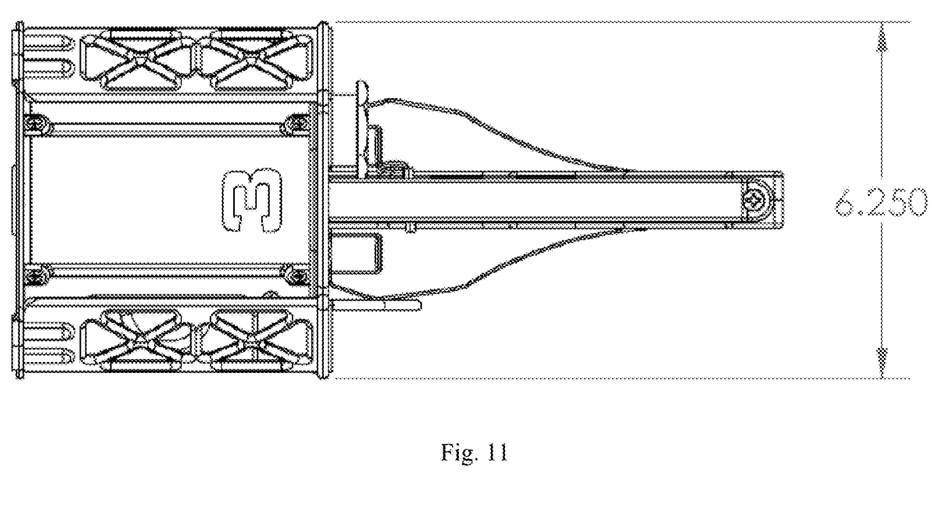
FIG. 11 is a bottom view of an embodiment of the present invention.

As depicted in FIG. 9-11, an embodiment of the device is ergonomically sized to have a handle width of roughly 1.00 inch, a height of roughly 7.66 inches, a total width of roughly 6.25 inches and a length of roughly 13.47 inches. These general dimensions ensure that the device is easily handled by a user in what may be a harsh environment.

Figure 13:
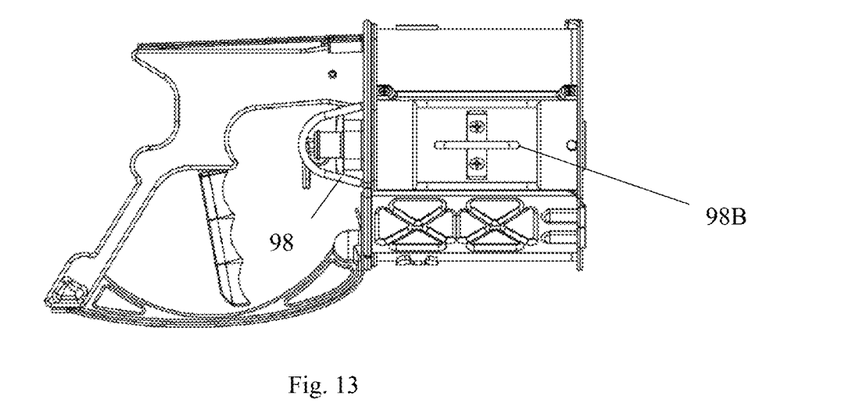
FIG. 13 is a side view of an embodiment of the present invention opposite from the side provided in FIG. 10.

As shown in FIGS. 12-13, both the handle assembly 10 and chamber housing 22 include lanyard attachment points 98A and 98B, respectively. Lanyard attachment points 98A, 98B are depicted as having a D-like shape, but may have any shape that provides an attachment point. Lanyard attachment points 98A, 98B ensure that handle assembly 10 and chamber housing 22 remain within control of an operator when disassembled.

An embodiment of the device also includes identifying indicia located on each housing to distinguish between each type of cartridge and/or the samples stored in each cartridge.

Glossary of Claim Terms

Alignment Member: is a structure that extends through the deck plate to come into contact with at least a portion of the base plate.

Alignment Member Receipt: is a structural feature sized and shaped to at least partially receive the alignment member.

Plunger: is a structure adapted to move relative to another object.

Sample Cartridge: is a mechanism adapted to take samples objects or scientific sample readings of a surrounding environment.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A sampling device, comprising:
   a handle assembly and a chamber housing;
   the handle assembly including:
      a trigger having a distal end and a proximal end and a pivot point disposed therebetween;
      a handle
      a rotational axle in mechanical communication with both the trigger and the handle, wherein the rotational axle passes through the pivot point in the trigger;
      a deck plate in mechanical communication with the handle, the deck plate having a central aperture sized to receive a quick-release pin;
      an alignment member extending at least partially through the deck plate;
      a guide receipt adapted to receive a guide support attached to a cover plate;
   the chamber housing further including:
      a base plate and an end plate, the base plate having a central aperture to receive the quick-release pin and an alignment member receipt to at least partially receive a portion of the alignment member when the alignment member extends through the deck plate;
      a plurality of chambers extending from the base plate towards the end plate;
      the end plate having a central aperture axially aligned with the central aperture in the base plate;
      the end plate and base plate being rotationally fixed with respect to each other;
      the cover plate disposed in overlying and abutting relation to a distal surface of the end plate, the cover plate having a central aperture axially aligned with the central aperture in the end plate;
      a fastening axle passing through the central aperture in the cover plate and the central aperture in the end plate such that the end plate remains free to rotate with respect to the cover plate, base plate, and chambers extending therebetween;
      a guide member extending from the cover plate in a proximal direction and sized to be received by the guide receipts in the handle assembly, wherein the guide member prevents rotation between the cover plate and the deck plate;
   an aperture in the deck plate that is axially aligned with a trigger action, the trigger action pin in communication with the distal end of the trigger, such that actuation of the trigger causes translation of the trigger action pin towards the chamber housing;
   a trigger pin receiving aperture disposed in the base plate; and
   a sample cartridge disposed within one of the plurality of chambers, the sample cartridge configured to open at a distal end and pass through a chamber aperture in the end plate, that is axially aligned with the trigger action pin, when the trigger action pin translates into the chamber through the trigger pin receiving aperture.

2. The sampling device of claim 1, further comprising the handle assembly and the chamber housing being detachable.

3. The sampling device of claim 1, further comprising a rotational bearing disposed in the central aperture in the end plate and a bearing disposed in the central aperture in the base plate.

4. The sampling device of claim 1, wherein at least one of the plurality of chambers is a designated empty chamber that does not include a sample cartridge.

5. The sampling device of claim 4, further comprising an attachment hard point secured to the designated empty chamber, the attachment hard point adapted to mechanically attach to a lanyard.

6. The sampling device of claim 1, further comprising the sample cartridge having a distal end that remains within its respective chamber when the trigger action pin is actuated and causes actuation of the sample cartridge.

7. The sampling device of claim 1, wherein the quick release pin has a position of repose in which a distal end of the pin extends through the apertures in the deck plate and the base plate.

8. The sampling device of claim 1, wherein the quick release pin has a release position in which a distal end of the pin does not protrude through the aperture in the base plate, thereby allowing the chamber housing to be separated from the handle assembly.

9. The sampling device of claim 1, further comprising chamber seals disposed at the distal end of each chamber, thereby sealing the chambers when the chamber seals are in abutting relation to the cover plate.

10. The sampling device of claim 1, further comprising a first plunger in the sample cartridge, wherein the first plunger is acted upon by the trigger action pin when the trigger action pin is axially aligned with the trigger pin receiving aperture and a user actuates the trigger.

11. The sampling device of claim 10, further comprising:
   a cartridge function spring disposed between the first plunger and a second plunger;
   a cartridge extension spring extending between the second plunger and a distal flange;
   whereby the translation of the trigger action pin through the trigger pin receiving aperture causes the trigger action pin to contact the first plunger, which causes the sample cartridge to open at a distal end, and further translation of the trigger action pin causes the first plunger to force the second plunger in a distal direction, which causes the distal end of the cartridge to extend through the aperture in the cover plate.

12. The sampling device of claim 1, further comprising a locking mechanism adapted to prevent rotation between the cover plate and collectively the base plate, chambers, and end plate.

13. A sampling device, comprising:
a handle assembly detachably coupled to a chamber housing;
the handle assembly including:
a handle with a trigger pivotally attached thereto;
a deck plate in mechanical communication with the handle, the deck plate having an aperture sized to receive a quick-release pin;
the chamber housing further including:
a base plate, the base plate having an aperture sized to receive the quick-release pin;
a plurality of chambers secured to and extending from the base plate in a distal direction;
a cover plate in mechanical communication with the chambers and the base plate in a rotationally free manner such that collectively the base plate and chambers can rotate with respect to the cover plate;
a guide member extending from the cover plate to the handle assembly thereby preventing rotation between the cover plate and the handle assembly;
a trigger action pin in communication with the trigger, such that actuation of the trigger causes translation of the trigger action pin towards the chamber housing;
an alignment member extending between the deck plate and the base plate, whereby the alignment member is configured to bring each chamber into operable alignment with the trigger action pin such that the trigger action pin can translate into one of the chambers when said chamber is in operable alignment with the trigger action pin; and
a sample cartridge disposed within one of the plurality of chambers, the sample cartridge configured to pass through an aperture in the end plate that is axially aligned with the sample cartridge when the trigger action pin translates into the chamber housing.

14. The sampling device of claim 13, wherein at least one of the plurality of chambers does not include a sample cartridge.

15. The sampling device of claim 13, wherein the quick release pin has a position of repose in which a distal end of the pin extends through the apertures in the deck plate and the base plate.

16. The sampling device of claim 13, wherein the quick release pin has a release position in which a distal end of the pin does not protrude through the aperture in the base plate, thereby allowing the chamber housing to be separated from the handle assembly.

17. The sampling device of claim 13, further comprising chamber seals disposed at the distal end of each chamber, thereby sealing the chambers when the chamber seals are in abutting relation to the cover plate.

18. The sampling device of claim 13, further comprising a locking mechanism adapted to prevent rotation between the cover plate and collectively the base plate, chambers, and end plate.

19. The sampling device of claim 13, further comprising a first plunger in the sample cartridge, wherein the first plunger is acted upon by the trigger action pin when the chamber housing the sample cartridge is in operable alignment with the trigger action pin and a user actuates the trigger.

20. The sampling device of claim 19, further comprising:
a cartridge function spring disposed between the first plunger and a second plunger;
a cartridge extension spring extending between the second plunger and a distal end;
whereby the translation of the trigger action pin through the trigger pin receiving aperture causes the trigger action pin to contact the first plunger, which causes the sample cartridge to open at the distal end, and further translation of the trigger action pin causes the first plunger to force the second plunger in a distal direction, which causes the distal end of the cartridge to extend through the aperture in the cover plate.

* * * * *